United States Patent [19]

Seiryo

[11] Patent Number: 5,151,190
[45] Date of Patent: Sep. 29, 1992

[54] METHOD FOR SEPARATING A LIQUID MIXTURE

[75] Inventor: Furuto Seiryo, Tokyo, Japan

[73] Assignees: Ryoka Techno Engineering & Construction Co.; Mitsubishi Kasei Corporation, both of Tokyo, Japan

[21] Appl. No.: 813,783

[22] Filed: Dec. 27, 1991

[30] Foreign Application Priority Data

Dec. 27, 1990 [JP] Japan ................................. 2-408428

[51] Int. Cl.$^5$ .............................................. B01D 61/36
[52] U.S. Cl. ..................... 210/640; 568/889; 568/917; 568/958
[58] Field of Search ............... 568/699, 899, 913, 917, 568/950, 958; 210/634, 640, 644, 649-654

[56] References Cited

U.S. PATENT DOCUMENTS

4,774,365 9/1988 Chen et al. .................... 568/699

Primary Examiner—Frank Sever
Attorney, Agent, or Firm—Oblon, Spivak, McClelland, Maier & Neustadt

[57] ABSTRACT

A method for separating water by pervaporation from a liquid mixture comprising isopropanol and water, which comprises (a) heating the liquid mixture, then supplying the heated mixture to a pervaporation membrane module unit using a polyimide-type separating membrane to conduct separation of the liquid mixture, recycling a part or whole of the liquid not permeated through the membrane to a feed liquid mixture, supplying a fresh feed liquid mixture to an optional place in the circulation route, and withdrawing the liquid mixture from an optional place in the circulation route, (b) controlling the amount of the liquid to be recycled among the liquid not permeated through the membrane to a level of at least 10 times by volume the amount of the fresh feed liquid mixture, and (c) controlling the difference between the liquid temperature at the inlet of the membrane module unit and the liquid temperature at the outlet of the membrane module unit to a level of at most 20° C.

11 Claims, 6 Drawing Sheets

METHOD FOR SEPARATING A LIQUID MIXTURE

BACKGROUND OF THE INVENTION

1. Field of the Invention

The present invention relates to a method for separating a liquid mixture by pervaporation. More particularly, the present invention relates to a method for recovering isopropanol of high purity by removing water from a water-containing isopropanol after being used for cleaning precision parts such as semiconductors.

2. Discussion of Background

As one of methods for separating liquid mixtures, so-called pervaporation is known wherein a certain specific component in a liquid mixture is separated by means of a membrane having a specific affinity with the component by placing the liquid mixture on one side (the primary side) of the membrane and vacuuming the other side (secondary side) by a vacuum pump or purging the secondary side with an inert gas so that the partial vapor pressure of the component passing through the secondary side is maintained to be lower than the equilibrium vapor pressure at the primary side.

This separation method is useful for separating a liquid mixture which can not be separated by a usual distillation method, such as an azeotropic mixture or a mixture of liquids having boiling points close to one another.

On the other hand, as a method for cleaning precision parts such as semiconductor wafers, it has been common in recent years to employ a method wherein such parts are cleaned with water, followed by cleaning with isopropanol (hereinafter referred to simply as IPA). In such a case, it has been attempted to remove water from the water-containing IPA after use to recover and reuse IPA of high purity. As the method for effectively separating water from the water-containing IPA, pervaporation may be considered.

In order to carry out this pervaporation method efficiently, it is advisable to maintain the temperature of the liquid mixture at a high level so that the equilibrium vapor pressure at the primary side will be high. However, the temperature of the liquid tends to decrease due to the latent heat of vaporization of the liquid. It is conceivable to increase the temperature of the liquid to be supplied to the membrane module unit, but such a method has a limitation in view of e.g. the heat resistance of the separating membrane. A method for efficiently supplying the heat corresponding to the latent heat of vaporization to the liquid mixture, is proposed, for example, in Japanese Examined Patent Publication No. 5441/1990 or No. 21288/1990. However, such a method is still inadequate from the viewpoint of the efficiency.

The apparatus for separating IPA and water used for cleaning semiconductor wafers, is desired to be incorporated in the production line for such wafers and accordingly is required to be as compact as possible and capable of treating the cleaning solution as much as possible. However, there has been no apparatus available which is compact and efficient enough to comply with such requirements.

SUMMARY OF THE INVENTION

The present inventors have conducted extensive researches to solve such problems and as a result have found it possible to design an efficient and compact separation apparatus by recycling a certain specific amount of a liquid not permeated through the membrane (hereinafter referred to as a "residual liquid"). The present invention has been accomplished on the basis of this discovery.

Thus, the present invention provides a method for separating water by pervaporation from a liquid mixture comprising isopropanol and water, which comprises (a) heating the liquid mixture, then supplying the heated mixture to a pervaporation membrane module unit using a polyimide-type separating membrane to conduct separation of the liquid mixture, recycling a part or whole of the liquid not permeated through the membrane to a feed liquid mixture, supplying a fresh feed liquid mixture to an optional place in the circulation route, and withdrawing the liquid mixture from an optional place in the circulation route, (b) controlling the amount of the liquid to be recycled among the liquid not permeated through the membrane to a level of at least 10 times by volume the amount of the fresh feed liquid mixture, and (c) controlling the difference between the liquid temperature at the inlet of the membrane module unit and the liquid temperature at the outlet of the membrane module unit to a level of at most 20° C., and a separation apparatus to be used for such a method.

BRIEF DESCRIPTION OF THE DRAWINGS

In the drawings, each of reference numerals 1, 17, 33, 49 and 65 indicates a heater for the liquid mixture, each of numerals 2, 18, 34, 50 and 66 indicates a module unit, each of 2a, 18a, 34a, 50a and 66a indicates a pervaporation membrane, each of numerals 3, 19, 35, 51 and 67 indicates a condenser for the permeated component, each of numerals 4, 20, 36, 52 and 68 indicates a vacuum pump at the secondary side, each f numerals 5, 21, 37 and 53 indicates a pump for recycling the liquid mixture, each of numerals 6, 22 and 38 indicates a valve to prevent reverse flow, and numeral 90 indicates a purge gas recycling device.

DETAILED DESCRIPTION OF THE PREFERRED EMBODIMENTS

Firstly, the pervaporation membrane module unit to be used in the present invention, will be described.

As the membrane module unit, any module unit useful for pervaporation, may be employed, and it is selected depending upon the liquid to be separated.

The separating membrane to be used for pervaporation is a diaphragm separating a compartment for the liquid to be treated and a compartment for the permeated vapor. With respect to the shape of the membrane, various types such as a sheet-form, a spiral-form, a tubular form and a hollow fiber form, may be employed depending upon the particular purpose. In the present invention, a hollow fiber type is particularly preferred, since it is thereby possible to take a large effective area of membrane per unit volume, and when pressure is exerted from outside the hollow fiber, a relatively high mechanical strength against high pressure can be obtained in spite of the thin tubular wall.

In the present invention, a polyimide-type separating membrane is employed as the separating membrane. Among polyimide-type separating membranes, preferred is a finely porous membrane made essentially of an aromatic polyimide, an aromatic polyamide imide or a mixture thereof. Such a membrane has imide bonds or amide bonds, and its affinity to water serves effectively at the time of selective separation of water, as intended by the present invention.

The aromatic polyimide to be used in the present invention is usually a condensation product of an aromatic diamine of the following formula (1) with an aromatic tetracarboxylic anhydride of the formula (2), which has repeating units of the formula (3):

$$H_2N-Ar'-NH_2 \quad (1)$$

(2)

(3)

In the above formulas, Ar' is a bivalent aromatic residue, preferably a phenyl, aryl, biphenyl, naphthyl or bisphenol residue which may be substituted, and Ar is a tetravalent aromatic tetracarboxylic acid residue.

The aromatic polyamide imide to be used in the present invention is usually the one having repeating units of the following formula (8):

(8)

In the formula (8), Ar' is as defined above.

In the present invention, there is no particular restriction as to such an aromatic polyimide, an aromatic polyamide imide or a mixture thereof (hereinafter referred to simply as an aromatic polyimide or the like of the present invention). However, from the viewpoint of the heat resistance, chemical resistance and durability, those disclosed in Japanese Unexamined Patent Publication No. 270506/1988 may be mentioned as preferred examples.

The inherent viscosity ($\eta_{inh}$) of the above copolyimide or copolyamideimide to be used in the present invention is selected within a range of at least 0.1 dl/g, more preferably from 0.3 to 4 dl/g (as measured in N-methylpyrrolidone at a concentration of 0.5% at 30° C.).

In the present invention, it is preferred to employ a composite separating membrane having a thin layer of a hydrophilic polymer coated on the above-mentioned finely porous membrane made of the aromatic polyimide or the like of the present invention, to improve the liquid permeation performance and separating performance.

As the hydrophilic polymer, a polyvinyl alcohol, an ethylene-vinyl alcohol copolymer, a water-soluble polyamide or a mixture thereof may be mentioned as a preferred example.

The polyvinyl alcohol to be used in the present invention is preferably a polyvinyl alcohol having an average degree of polymerization of from 500 to 3500 and a saponification degree of from 80 to 100 mol% or its copolymer, and it includes polyvinyl alcohol copolymers (block copolymers and graft copolymers) such as a carboxyl-modified polyvinyl alcohol having COONa groups introduced as functional groups by copolymerizing and saponifying an unsaturated carboxylic acid such as acrylic acid, crotonic acid, maleic acid or itaconic acid or its ester with vinyl acetate, a cation-modified polyvinyl alcohol obtained by copolymerizing and saponifying an amino alkyl methacrylamide-type monomer with vinyl acetate, a Si-modified polyvinyl alcohol obtained by copolymerizing and saponifying a Si group-containing vinyl polymer with vinyl acetate and an acetoacetyl-modified polyvinyl alcohol having reactive functional groups in its molecule.

The soluble polyamide of the present invention may be a polyamide having the crystallinity reduced and the solubility improved by selecting the monomers for copolymerization, by modifying the compositional proportions or by introducing side chains to a polyamide. Specifically, it includes a polyamide having an N-alkylamide, a polyamide made of a sulfonic acid derivative, a polyamide having ether bonds in its molecule, a polyamide having alkoxy groups, a polyamide obtained by copolymerizing a lactam and a polyol, a copolymer polyamide such as nylon 6/66/12 or nylon 6/66/610, a multi-component copolymer polyamide having an aliphatic ring or a hetero ring such as a piperazine ring, a pyridine ring or a furan ring as a cyclic secondary amine introduced in its molecule and those disclosed in "Industrial Materials" vol. 33, No. 1, p 133-137. As specific examples of such a water-soluble polyamide, those disclosed in Japanese Unexamined Patent Publication No. 126925/1990, may be mentioned.

The ethylene-vinyl alcohol copolymer resin to be used in the present invention preferably has an ethylene content within a range of from 10 to 60 mol% and a saponification degree of from 60 to 100 mol%. To the ethylene-vinyl alcohol copolymer, an α-olefin such as propylene, α-butene, α-pentene, α-hexene, α-heptene, α-octene, α-nonene, α-decene, α-pentadecene, α-hexadecene, α-octadecene or α-eicosene, may be copolymerized as a copolymer component as a third component. The ethylene-vinyl alcohol copolymer resin of the present invention further includes a carboxyl-modified ethylene-vinyl alcohol copolymer having COONa groups introduced as functional groups by copolymerizing and saponifying an unsaturated carboxylic acid such as acrylic acid, maleic acid or itaconic acid, or its ester, with an ethylene-vinyl acetate, a cation-modified copolymer obtained by copolymerizing and saponifying an aminoalkyl methacrylamide-type monomer with an ethylene vinyl acetate, a Si-modified copolymer obtained by copolymerizing and saponifying a Si group-containing vinyl monomer with an ethylene-vinyl acetate, and an acetoacetyl-modified copolymer having reactive functional groups in its molecule.

The finely porous film made of an aromatic polyimide or the like of the present invention can readily be produced by a conventional film-forming method such as a dry system film-forming method, a wet system film-forming method or an extraction method. Preferably, a wet system film-forming method is employed. For example, an asymmetric finely porous film having a skin layer on its surface is particularly preferred which is obtainable in such a manner that a thin film is formed from a polymer dope, solidified in a poor solvent such as water and then thoroughly washed and dried. The finely porous film to be used in the present invention preferably has a pore size of from 5 Å to 1 μm, a steam permeation rate of at least $10^{-4}$ cm$^3$/cm$^2$·sec cmHg and a ratio of the permeation rate of hydrogen to the permeation rate of nitrogen gas of at least 2.5 and a film thickness of from 10 to 500 μm. In the case of a hollow fiber membrane, the outer diameter is preferably from 100 to 3000 μm.

The finely porous film of an aromatic polyimide or an aromatic polyamide imide which is preferably employed in the present invention, may be prepared, for example, in accordance with the methods for the preparation of separating membranes disclosed in Japanese Unexamined Patent Publications No. 231017/1987, No. 175116/1988 and No. 175115/1988.

As a method for forming a thin layer of a hydrophilic polymer of the present invention on the finely porous film, a method of coating the finely porous film with a dilute solution having a hydrophilic polymer dissolved in a solvent or a method by plasma polymerization, may be mentioned. As the coating method, a conventional method such as a dipping method, a doctor blade method, a bar coater method, a roll transferring method or a spray method may be employed. For coating the hollow fiber finely porous film, the dipping method is particularly preferred. The coating may be applied either one or both of the inner and outer surfaces of the hollow fiber. The solvent to be used for the preparation of the dilute solution of the hydrophilic polymer is not particularly limited so long as it is a solvent capable of dissolving the hydrophilic polymer and it is a poor solvent to the finely porous film. As a particularly preferred solvent, water, alcohol or a solvent mixture of water/alcohol, may be mentioned. The polymer concentration is suitably adjusted depending upon the pore structure or the permeation performance of the finely porous film to be used, and it is preferably from 0.05 to 10% by weight.

The thickness of the thin layer obtained by the hydrophilic polymer is usually from 100 Å to 50 μm, preferably from 500 Å to 5 μm.

When the composite separating membrane of the present invention is used in the field where chemical resistance is required, such as for dehydration of an organic solvent by a pervaporation membrane, it is preferred to use the hydrophilic polymer in the form crosslinked by a crosslinking agent. The crosslinking of the hydrophilic polymer may be conducted, for example, by a method wherein the crosslinking agent is incorporated in a dilute solution of the hydrophilic polymer, and the solution is coated on the finely porous film, then dried and subjected to heat treatment at a temperature of from −50° to 300° C., preferably from 100° to 200° C. The crosslinking agent to be used, is not particularly limited. However, preferred are formalin, an organic acid, a dialdehyde, a melamine resin and a block isocyanate. The crosslinking may be conducted also by a method wherein the composite separating membrane is subjected to heat treatment within a temperature range of at least 150° C., preferably from 180° to 225° C. Namely, the hydrophilic polymer is thereby converted to be hot water-insoluble. If the temperature for this heat treatment is too low, the insolubilization will be inadequate, and if the temperature is too high, a heat deterioration will result. The degree of crosslinking is adjusted depending upon the desired chemical resistance to the organic solvent to be used for pervaporation.

In order to improve the adhesion between the hydrophilic polymer and the finely porous film, it is preferred to treat the surface of the finely porous film with a silane coupling agent before the formation of the hydrophilic polymer layer on the finely porous film. As such a silane coupling agent, $\gamma$-ureidopropyltriethoxysilane, (aminopropyl-triethoxysilane or N-$\beta$-(aminoethyl)-$\gamma$-aminopropyltrimethoxysilane, is particularly preferred. The treatment with the silane coupling agent is conducted in such a manner that an alcohol solution or an aqueous solution of a silane coupling agent is coated on the finely porous film by a dipping method or a spraying method, then the polymer solution is coated on the finely porous film, followed by heat treatment at a temperature of at least 100° C., preferably at least 150° C., more preferably at least 180° C. Otherwise, a silane coupling agent may be incorporated to the polymer solution, and such a solution is coated on the surface of the finely porous film. In this case, the silane coupling agent is used in the form of a solution in water, in water/alcohol, or in an alcohol having a concentration of the silane coupling agent of from 0.001 to 5% by weight.

If the temperature for the heat treatment of the composite membrane is lower than 150° C., the effect of the silane coupling agent for adhesion treatment sometimes tends to be poor.

In order to attain a high separation ratio by the composite separating membrane composed of the hydrophilic polymer and the aromatic polyimide or the like of the present invention, the separation factor of the finely porous film of the aromatic polyimide or the aromatic polyamide imide is at least 1.0, preferably at least 1.8 at a weight ratio of water/IPA =13/87 at a temperature of 80° C. at a vacuum degree of 5 Torr. On the other hand, if the separation factor of the hydrophilic polymer is too high, the permeation rate will be low, and depending upon the thickness of the hydrophilic polymer layer, the permeation rate tends to be extremely low, such being undesirable. Accordingly, in order to attain permeation performance with both the separation ratio and the permeation rate being well balanced, it is preferred to select the hydrophilic polymer so that the separation factor of a homogeneous film composed solely of the aromatic polyimide or the like of the present invention, is higher by at least 10%, more preferably at least two times, than the separation factor of a homogeneous film composed solely of the hydrophilic polymer. These separation factors are characteristic values evaluated with respect to homogeneous films (non-porous films) of from 20 to 30 μm at a weight ratio of water/IPA =13/87 at a temperature of 80° C. at a vacuum degree of 5 Torr.

Now, the separation method of the present invention will be described.

Figure 1:
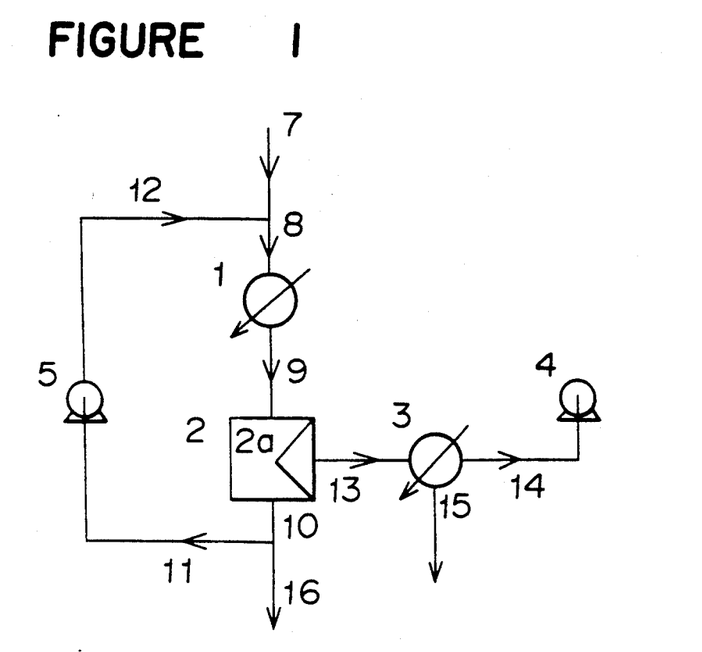
FIG. 1 is a process flowchart of one embodiment of the present invention and represents also a process flowchart of Example 1.

FIG. 1 illustrates one embodiment of the process flowchart of the present invention.

A fresh feed liquid mixture is supplied from a pipe line 7. The liquid mixture heated by a heater 1 is supplied via a pipe line 9 to a pervaporation membrane module unit 2.

Of the liquid mixture, the component (water) having an affinity with the separating membrane will penetrate and permeate through a separating membrane 2a, then will evaporate at the secondary side and will be condensed in a condenser 3 and withdrawn from a pipe line 15.

On the other hand, a part of the residual liquid having the component (IPA) having a small affinity with the separating membrane 2a concentrated, is withdrawn via a pipe line 16 out of the system, and the rest is recycled via a pipe line 11 and a recycling pump 5 and combined to a feed liquid mixture at point 8 and again supplied to the heater 1.

The amount of the liquid recycled via the pipe line 11 is at least 10 times, preferably at least 15 times, more preferably at least 20 times, by volume, the amount of the liquid supplied afresh from the pipe line 7. If the amount of the liquid recycled is small, the effect for improving the performance tends to be inadequate.

In the present invention, the difference between the liquid temperature at the inlet and the liquid temperature at the outlet of the membrane module unit, i.e. the difference in the liquid temperature between the pipe line 9 and the pipe line 10, is required to be at most 20° C., preferably at most 15° C., more preferably at most 12° C. If the difference between the liquid temperature at the inlet and the liquid temperature at the outlet of the membrane module unit (hereinafter referred to as a "temperature drop") is large, the equilibrium vapor pressure at the primary side lowers, whereby the permeable amount decreases, such being undesirable.

Figure 2:
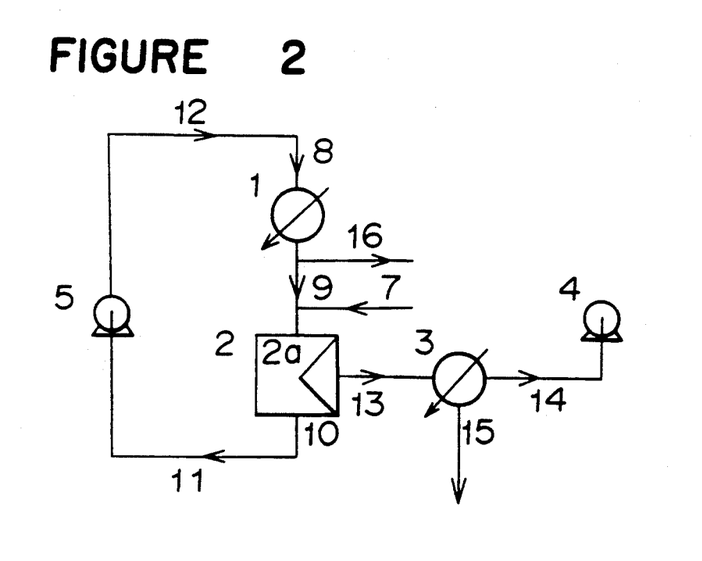
FIG. 2 is a process flowchart showing an embodiment wherein the place at which fresh feed liquid mixture is supplied to the circulation route and the place at which a concentrated liquid of the component hardly permeable through the membrane is withdrawn is different from FIG. 1.

The supply of a fresh feed liquid mixture to the circulation route and the withdrawal of a part of the concentrated liquid of the component hardly permeable through the membrane, can be made at optional places in the circulation route. For example, the case as illustrated in FIG. 2 is one of the preferred embodiments of the present invention.

Figure 3:
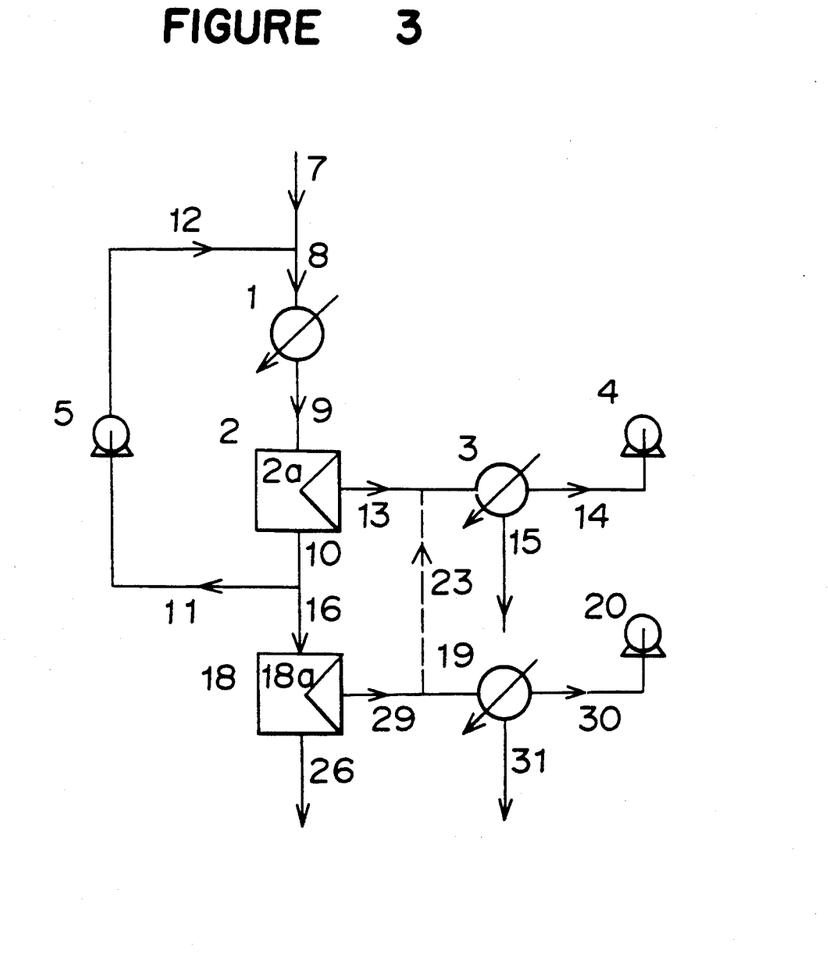
FIG. 3 illustrates an embodiment wherein a residual liquid is supplied to another pervaporation module unit and represents also a process flowchart of Example 2.
Figure 4:
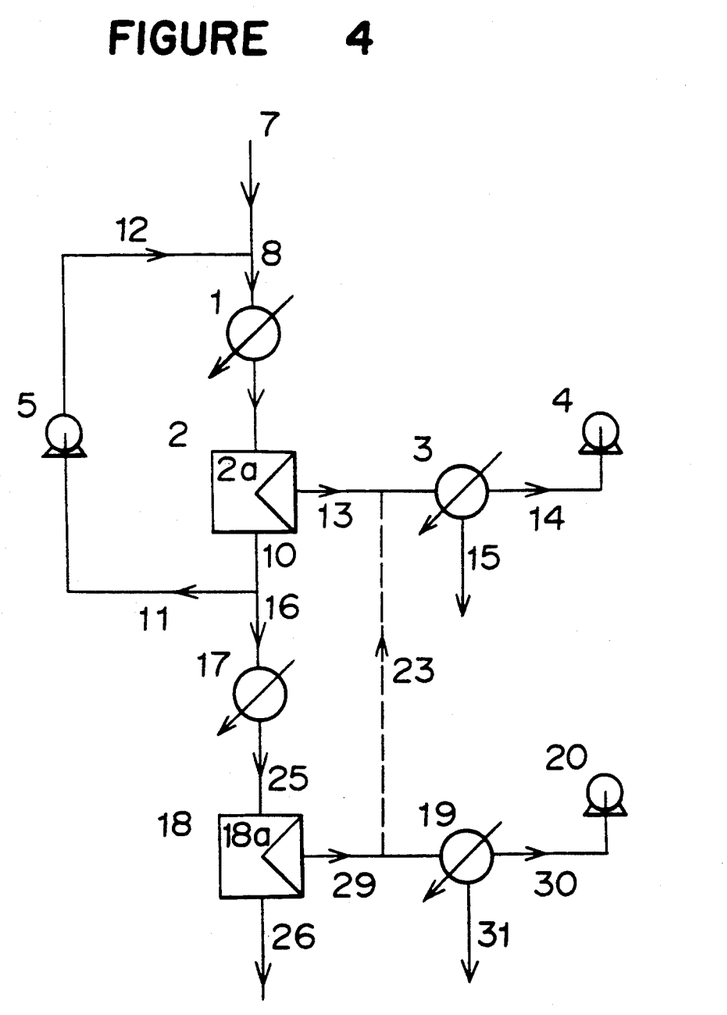
FIG. 4 is a process flowchart illustrating an embodiment wherein the residual liquid is heated and then supplied to another pervaporation module unit.
Figure 5:
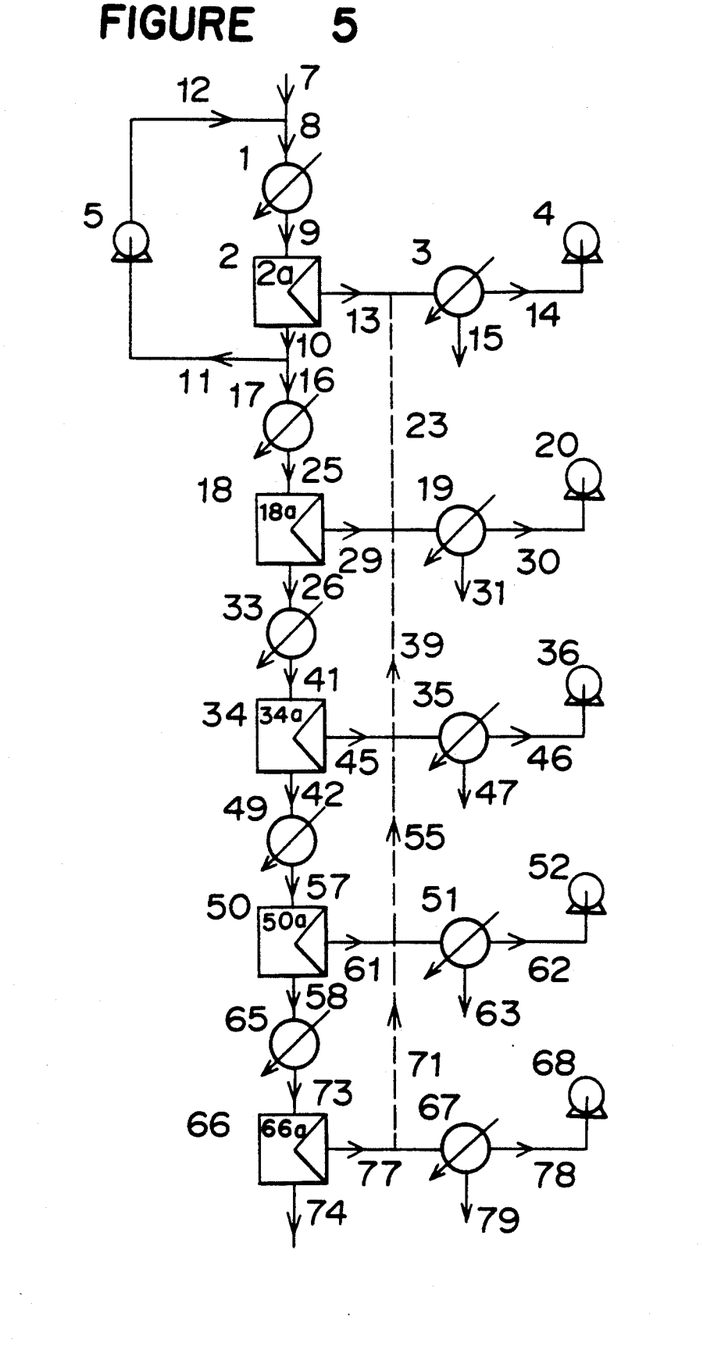
FIG. 5 is a process flowchart illustrating an embodiment wherein the residual liquid is heated and then supplied to a multi-stage pervaporation system.
Figure 6:
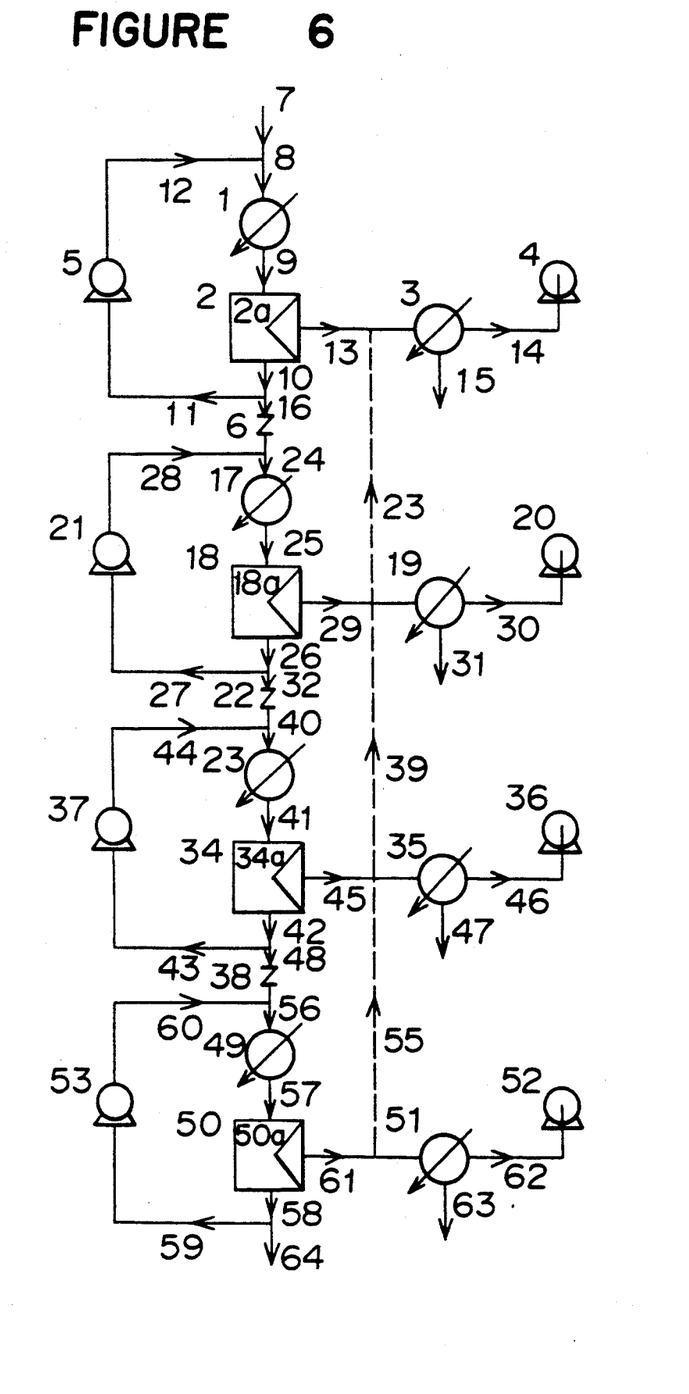
FIG. 6 is a process flowchart illustrating a manner in which the apparatus for the separation method of the present invention are connected in series to form a multi-stage system.
Figure 7:
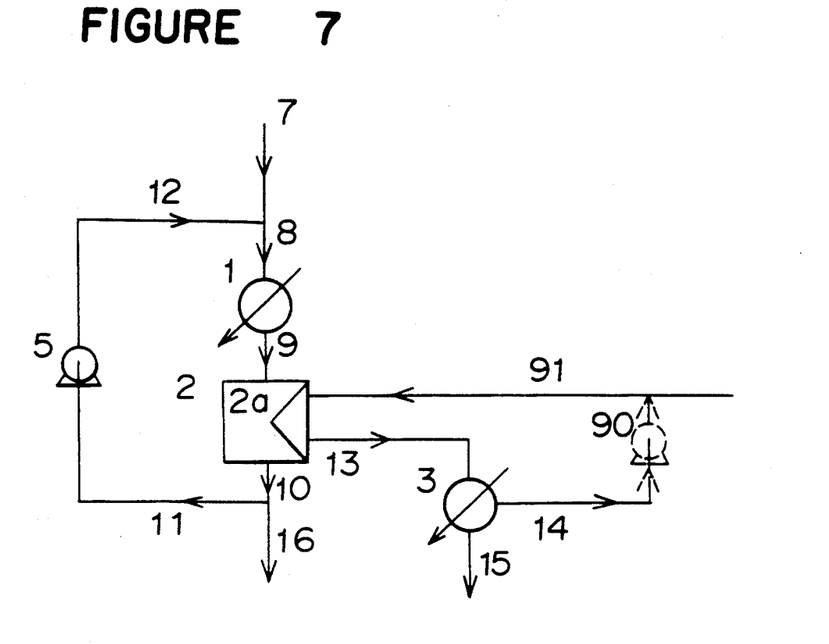
FIG. 7 is a process flowchart showing a method for purging the permeated vapor at the secondary side.

Further, the present invention includes a method wherein, as shown in FIG. 3, the residual liquid withdrawn from the pipe line 16 out of the first stage membrane module unit, is supplied further to a pervaporation membrane module unit 18, a method wherein, as shown in FIG. 4 or 5, the residual liquid withdrawn from the pipe line 16 out of the first stage membrane module unit, is heated by a heater 17 and then supplied further to a pervaporation membrane module unit, a method wherein, as shown in FIG. 6, separation apparatus as shown in FIG. 1 are connected in series to form a multi-stage system, and a method wherein, as shown in FIG. 7, an inert gas (such as nitrogen or argon) which is different from the permeated vapor, is supplied from a pipe line 91 to purge the permeated vapor.

Further, the vacuum pump 4 may be not only a mechanical vacuum pump but also a vacuum means employing a vapor ejector.

The method of the present invention has a remarkable feature that a part of the residual liquid is recycled to increase the amount of the liquid to be supplied to the membrane module unit.

If the amount of the liquid which permeates through the separating membrane, is the same, the quantity of the latent heat of vaporization taken from the liquid mixture at the primary side is the same. Therefore, the temperature drop of the liquid supplied to the membrane module unit is substantially inversely proportional to the amount of the feed liquid.

Accordingly, the larger the amount of the recycled liquid, the better the prevention of the temperature drop, and the larger the amount of permeation.

Therefore, in the present invention, the amount of the liquid to be recycled is usually at least 10 times, preferably at least 15 times, by volume, the amount of the liquid supplied from the pipe line 7.

Further, the temperature drop of the liquid due to the latent heat of vaporization differs depending upon the type of the liquid and the mixing ratio. Therefore, it is necessary to control the amount of the liquid to be recycled, etc. so that the temperature drop of the liquid would be at most 20° C.

The separation method of the present invention is particularly useful for the recovery of IPA of high purity by removing water from used IPA containing water after being used for cleaning precision parts such as semiconductors. When the method of the present invention is used for the recovery of such used IPA, the liquid mixture supplied afresh is a liquid mixture comprising IPA and water, which usually has a water content of at most about 50% by weight, preferably at most about 20% by weight, more preferably at most 10%.

As the concentrated residual liquid, IPA of high purity is obtained which usually has a water content of at most 13% by weight, preferably at most 10% by weight, more preferably at most 5% by weight, most preferably at most 1% by weight.

A mixture having a water content of 13% (IPA concentration of 87%) is a so-called azeotropic mixture. If the mixture has a higher water content, it is possible to remove water by distillation. However, with a mixture having a water content of less than 13%, it is difficult to remove water by distillation. The present invention provides an effective method whereby IPA having a relatively low water content can be further dehydrated to obtain IPA of high purity.

Further, according to the method of the present invention, it is possible to regenerate IPA of a constant purity by adjusting the amount of the recycled liquid, even when the water content of the liquid mixture supplied afresh, has changed.

Precision parts to which the method of the present invention may be applied include semiconductor parts such as wafers, liquid crystals, display device elements, hard discs, lenses, magnetic heads, thermal heads and quartz oscillators. The method of the present invention can be used not only for cleaning such precision parts but also for water removal or drying.

Further, the method of the present invention can be used not only for the recovery of IPA used for cleaning precision parts, but also for dehydration and recovery of IPA after being used for medical or coating purposes.

Now, the present invention will be described in further detail with reference to Examples. However, it should be understood that the present invention is by no means restricted by such specific Examples.

COMPARATIVE EXAMPLE 1

A membrane module unit having a permeation area of 10 m$^2$ was prepared by using as a pervaporation membrane a composite membrane having a polyvinyl alcohol coated on a polyimide resin.

Figure 8:
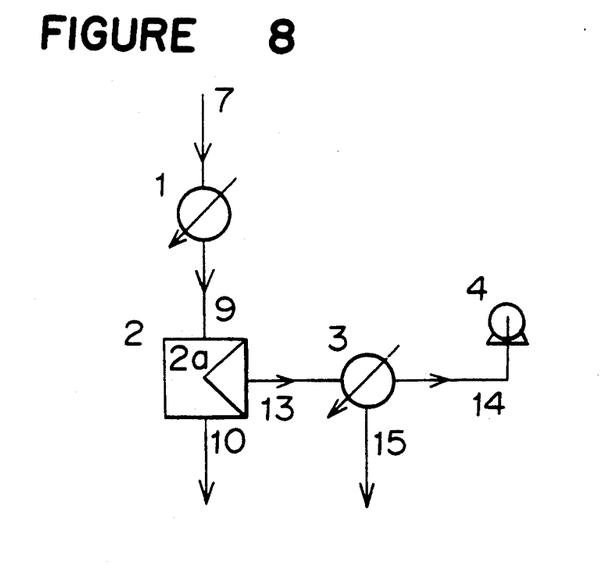
FIG. 8 is a process flowchart illustrating Comparative Example 1.

Using this module unit, a separation apparatus as shown in FIG. 8 was assembled. The temperature at the inlet of the module unit was maintained at 70° C., and the pressure at the secondary side was maintained at 10 Torr by a vacuum pump 4.

Referring to the apparatus shown in FIG. 8, an aqueous solution containing 50% by weight of IPA (isopropyl alcohol) was supplied as the liquid mixture supplied from the pipe line 7 in an amount of 10.8 l/hr, whereby the temperature of the residual liquid obtained from the outlet 10 of the module unit was 19° C., and the IPA concentration was 54.5% by weight.

The amount of the permeated liquid in this case was 0.81 l/hr, and the IPA concentration of the permeated liquid was 0.013% by weight.

EXAMPLE 1

Using the same module unit as used in Comparative Example 1, a separation apparatus as shown in FIG. 1 was assembled. The amount of the liquid recycled by the pump 5 was adjusted to a level of 980 l/hr, and other conditions were maintained to be the same as in Comparative Example 1.

Namely, the temperature at the inlet of the module unit was maintained at 70° C., and the pressure at the secondary side was maintained at 10 Torr. The amount of the aqueous IPA solution supplied from the pipe line 7 was 10.8 l/hr and the concentration was 50% by weight.

Under these conditions, the apparatus of FIG. 1 was operated, whereby the liquid temperature at the outlet of the module unit was 65° C., and the IPA concentration of the residual liquid withdrawn from the pipe line 16 was 90.6% by weight.

In this case, the amount of the permeated liquid was 4.4 l/hr, and the IPA concentration in the permeated liquid was 0.025% by weight.

As compared with Comparative Example 1, Example 1 was superior by 4.4 l/0.81 l=5.4 times in the amount of the permeated liquid and a concentration effect of (90.6−50.0)/(54.5−50.0)/(54.5−50.0)=9.0 times in terms of the increase in the concentration of the residual liquid.

EXAMPLE 2

Using the same module unit as used in Comparative Example 1, a separation apparatus as shown in FIG. 3 was assembled. The operational conditions of the first stage module unit were adjusted to be the same as Example 1. Namely, the temperature at the inlet of the first stage module unit was maintained at 70° C., and the pressure at the secondary side was maintained at 10 Torr. The amount of the aqueous IPA solution supplied from the pipe line 7 was 10.8 l/hr, and the concentration was 50% by weight. The amount of the liquid recycled by the pump 5 was adjusted at a level of 980 l/hr.

The secondary side pressure of the second stage module unit was adjusted at 10 Torr like the first stage, and the inlet temperature was adjusted to be equal as the outlet temperature of the first stage module unit.

Under these conditions, the apparatus of FIG. 3 was operated, whereby the temperature of the residual liquid of the second stage module unit (the liquid temperature in the pipe line 26) was 27° C., and the IPA concentration was 94.6% by weight.

The total amount of the permeated liquid of the first and second stages was 4.6 l/hr, and the IPA concentration of the permeated liquid was 0.028% by weight.

As compared with Comparative Example 1, Example 2 was superior by 4.6 l/0.81 l=5.7 times in the amount of the permeated liquid and a concentration effect of (94.9−50.0)/(54.5−50.0)=10 times in terms of the increase in the concentration of the residual liquid.

EXAMPLES 3 to 6 and COMPARATIVE EXAMPLES 2 to 6

The operation in each case was conducted in the same manner as in Example 1 except that the permeation area of the membrane and the amount of the recycled liquid were changed as identified in Table 1. The results are shown in Table 1.

TABLE 1

| | Permeation area of the membrane | Feed liquid (F kg/h) | Recycled liquid (R kg/h) | R/F | Liquid temp (°C.) Inlet | Outlet | Difference | Permeated liquid Amount (kg/h) | Ratio |
|---|---|---|---|---|---|---|---|---|---|
| Comp. Ex. 2 | 50 m$^2$ | 9.8 | 45.1 | 4.6 | 70 | 20.6 | 49.4 | 3.65 | 1 |
| Comp. Ex. 3 | 50 m$^2$ | 9.8 | 78.9 | 8.1 | 70 | 29.4 | 40.6 | 4.42 | 1.21 |
| Comp. Ex. 4 | 50 m$^2$ | 9.8 | 184.6 | 18.8 | 70 | 48.8 | 21.2 | 4.77 | 1.31 |
| Ex. 3 | 50 m$^2$ | 9.8 | 366.3 | 37.4 | 70 | 58.9 | 11.1 | 4.81 | 1.32 |
| Ex. 4 | 50 m$^2$ | 9.8 | 731.4 | 74.6 | 70 | 64.3 | 5.7 | 4.81 | 1.32 |
| Ex. 5 | 10 m$^2$ | 5.38 | 71.89 | 13.4 | 110 | 104.5 | 5.5 | 0.477 | 1 |
| Comp. Ex. 5 | 10 m$^2$ | 9.8 | 51.8 | 5.3 | 70 | 39.2 | 30.8 | 2.77 | 1 |
| Comp. Ex. 6 | 10 m$^2$ | 9.8 | 92.7 | 9.5 | 70 | 45.4 | 24.6 | 3.48 | 1.26 |
| Ex. 6 | 10 m$^2$ | 9.8 | 793.5 | 81.0 | 70 | 65.6 | 4.4 | 4.39 | 1.58 |

| Concentration (wt %) | Concentration difference (wt %) | Concentration ratio water | Pressure at secondary |
|---|---|---|---|

TABLE 1-continued

|  | Inlet | Outlet | Solvent | Water | (solvent) | side (Torr) |
|---|---|---|---|---|---|---|
| Comp. Ex. 2 | 50 | 79.7 | 27.9 | 20.3 | 1 (1) | 10 |
| Comp. Ex. 3 | 50 | 91.07 | 41.1 | 8.93 | 2.27 (1.38) | 10 |
| Comp. Ex. 4 | 50 | 97.33 | 47.33 | 2.67 | 7.60 (1.59) | 10 |
| Ex. 3 | 50 | 98.0 | 48.10 | 1.90 | 10.7 (1.61) | 10 |
| Ex. 4 | 50 | 98.25 | 48.25 | 1.75 | 11.6 (1.62) | 10 |
| Ex. 5 | 91.07 | 99.923 | 8.853 | 0.077 | 263.6 (3.35) | 5 |
| Comp. Ex. 5 | 50 | 69.7 | 19.7 | 30.3 | 1 (30.3) | 10 |
| Comp. Ex. 6 | 50 | 77.5 | 27.5 | 22.5 | 1.35 (22.5) | 10 |
| Ex. 6 | 50 | 90.56 | 40.56 | 9.44 | 3.21 (9.44) | 10 |

As described in the foregoing, according to the present invention, the liquid separation by pervaporation can be conducted efficiently. Further, it is thereby possible to efficiently recover and reuse isopropanol used for cleaning precision parts, whereby an environmental problem can be reduced.

What is claimed is:

1. A method for separating water by pervaporation from a liquid mixture comprising isopropanol and water, which comprises (a) heating the liquid mixture, then supplying the heated mixture to a pervaporation membrane module unit using a polyimide-type separating membrane to conduct separation of the liquid mixture, recycling a part or whole of the liquid not permeated through the membrane to a feed liquid mixture, supplying a fresh feed liquid mixture to an optional place in the circulation route, and withdrawing the liquid mixture from an optional place in the circulation route, (b) controlling the amount of the liquid to be recycled among the liquid not permeated through the membrane to a level of at least 10 times by volume the amount of the fresh feed liquid mixture, and (c) controlling the difference between the liquid temperature at the inlet of the membrane module unit and the liquid temperature at the outlet of the membrane module unit to a level of at most 20° C.

2. The method according to claim 1, wherein the amount of the liquid to be recycled among the liquid not permeated through the membrane is adjusted to a level of 15 times by volume the amount of the fresh feed liquid mixture.

3. The method according to claim 1, wherein the difference between the liquid temperature at the inlet of the membrane module unit and the liquid temperature at the outlet of the membrane module unit, is adjusted to a level of at most 15° C.

4. The method according to claim 1, wherein the polyimide-type separating membrane is a hollow fiber membrane.

5. The method according to claim 1, wherein the polyimide-type membrane is a composite separating membrane comprising a thin layer of an aromatic polyimide, an aromatic polyamide imide or a mixture thereof.

6. The method according to claim 5, wherein the composite separating membrane has a thin layer of a hydrophilic polymer formed on a finely porous film of an aromatic polyimide, an aromatic polyamide imide or a mixture thereof.

7. The method according to claim 6, wherein the hydrophilic polymer is selected so that the separation factor of a homogeneous film made solely of the aromatic polyimide or the aromatic polyamide imide is higher by at least 10% than the separation factor of a homogeneous film made solely of the hydrophilic polymer, as measured by a pervaporation method at a weight ratio of water/isopropanol = 13/87 at a temperature of 80° C. at a vacuum degree of 5 Torr.

8. The method according to claim 6, wherein the hydrophilic polymer is selected from the group consisting of a polyvinyl alcohol, an ethylene-vinyl acetate copolymer saponification product, a polyamide and a mixture thereof.

9. The method according to claim 6, wherein the surface of the finely porous film is treated with a silane coupling agent.

10. A method for recovering isopropanol of high purity by removing water by pervaporation from a liquid mixture comprising water and isopropanol used for cleaning precision parts, which comprises (a) heating the liquid mixture, then supplying the heated mixture to a pervaporation membrane module unit using a polyimide-type separating membrane to conduct separation of the liquid mixture, recycling a part or whole of the liquid not permeated through the membrane to a feed liquid mixture, supplying a fresh feed liquid mixture to an optional place in the circulation route, and withdrawing the liquid mixture from an optional place in the circulation route, (b) controlling the amount of the liquid to be recycled among the liquid not permeated through the membrane to a level of at least 10 times by volume the amount of the fresh feed liquid mixture, and (c) controlling the difference between the liquid temperature at the inlet of the membrane module unit and the liquid temperature at the outlet of the membrane module unit to a level of at most 20° C.

11. The method according to claim 10, wherein isopropanol of high purity is isopropanol having a water content of not more than 10%.

* * * * *